(12) United States Patent
Ventresque et al.

(10) Patent No.: US 7,216,529 B2
(45) Date of Patent: May 15, 2007

(54) METHOD FOR CONTROLLING THE INTEGRITY OF A NANOFILTRATION OR REVERSE OSMOSIS MODULE, OR MODULE SYSTEM

(75) Inventors: Claire Ventresque, Colombes (FR); Valerie Gisclon-Lallemand, Poissy (FR); Guy Bablon, Feucherolles (FR); Gérard Chagneau, Paris (FR)

(73) Assignees: Veolia Eau - Compagnie Generale des Eaux, Paris (FR); Syndicat des Eaux d'ile de France (SEDIF), Paris (FR)

( * ) Notice: Subject to any disclaimer, the term of this patent is extended or adjusted under 35 U.S.C. 154(b) by 225 days.

(21) Appl. No.: 10/297,050

(22) PCT Filed: Jun. 1, 2001

(86) PCT No.: PCT/FR01/01713

§ 371 (c)(1),
(2), (4) Date: Jun. 16, 2003

(87) PCT Pub. No.: WO01/91891

PCT Pub. Date: Dec. 6, 2001

(65) Prior Publication Data

US 2004/0020858 A1    Feb. 5, 2004

(30) Foreign Application Priority Data

Jun. 2, 2000    (FR) ................................. 00 07106

(51) Int. Cl.
*G01M 3/04* (2006.01)
*B01D 61/10* (2006.01)

(52) U.S. Cl. .............................. 73/40; 73/38; 210/650; 210/652; 210/739

(58) Field of Classification Search ................ 210/650, 210/652, 739, 85, 94, 96.2, 745; 73/38, 40, 73/40.7
See application file for complete search history.

(56) References Cited

U.S. PATENT DOCUMENTS 3,873,653 A * 3/1975 Meinecke et al. ............. 264/41

(Continued)

FOREIGN PATENT DOCUMENTS

JP    2000-107575    *    4/2000

(Continued)

OTHER PUBLICATIONS

Internet Publication: "Membrane life in a seeded-slurry reverse osmosis system", GJG Juby and CF Schuette, Water SA vol. 26 No. 2 Apr. 2000, pp. 239-248.*

*Primary Examiner*—Joseph Drodge
(74) *Attorney, Agent, or Firm*—Browdy and Neimark, PLLC (57) ABSTRACT

The invention concerns a method for controlling a nanofiltration or reverse osmosis module system designed for treating a supply fluid or for detecting living micro-organism leaks, each module comprising nanofiltration or reverse osmosis membranes and joints connecting said membranes, including steps which consist in: selecting in the supply fluid a dissolved compound present in significant amount but normally highly retained by the membranes; measuring the concentration value of said compound in a downstream zone of a module of said system; comparing said measured value with a reference value; and recognising the existence of a fault in said zone of the system when said measured value is higher than the reference value.

15 Claims, 8 Drawing Sheets

U.S. PATENT DOCUMENTS

| | | | |
|---|---|---|---|
| 4,188,817 A | * | 2/1980 | Steigelmann ................ 73/40.7 |
| 5,411,889 A | * | 5/1995 | Hoots et al. .................... 436/6 |
| 5,905,197 A | * | 5/1999 | Wilf .............................. 73/86 |
| 6,370,943 B1 | | 4/2002 | Glucina et al. |
| 6,568,282 B1 | * | 5/2003 | Ganzi ...................... 73/861.42 |

FOREIGN PATENT DOCUMENTS

WO     WO 99/44728 A1     9/1999

\* cited by examiner

METHOD FOR CONTROLLING THE INTEGRITY OF A NANOFILTRATION OR REVERSE OSMOSIS MODULE, OR MODULE SYSTEM

FIELD OF THE INVENTION

The present invention relates to a method adapted to check the integrity of systems of nanofiltration or reverse osmosis modules such as those which are used in the processes or separation and concentration of solutions, in particular in the field of water treatment.

BACKGROUND OF THE INVENTION

The technique of water purification supplied by membranes has an increasing number of industrial implementations of all capacities. The fields of membrane filtration techniques overlap but are generally divided into:

- microfiltration, in the region of pore diameters of approximately 0.5 µm,
- ultrafiltration, in the region of pore diameters of approximately 10 nm,
- nanofiltration, having a cut-off capability of around 1 nanometer or 250 daltons (in practice from 200 to 300 daltons for nanofiltration membranes currently on the market),
- reverse osmosis below 1 nanometer.

Nanofiltration makes it possible to eliminate a substantial proportion of the dissolved organic pollution and certain mineral ions. More particularly, it enables soluble organic minerals and certain mineral ions of quite large "apparent" size. On account of this, nanofiltration overlaps the field of reverse osmosis. Nanofiltration is also referred to as "low pressure reverse osmosis" or "hyperfiltration".

Due to its very low cut-off thresholds, nanofiltration ensures total microbial sterility.

Nevertheless, in industrial installations, nanofiltration membranes are mounted within nanofiltration modules, and these nanofiltration modules are themselves implemented by virtue of arrangements of a high number of modules capable of ensuring the required throughput. Thus, even though nanofiltration is inherently impermeable to bacteria and viruses at membrane level, the arrangement of a high number of modules may include connection defects which put in doubt the impermeability of the modules.

Furthermore, the possibility always exists of modules that are defective or badly constructed (poor glued joints of the membranes, holes not detected in the membrane, etc.).

There are two general configurations commonly used to mount nanofiltration membranes within a module:

- a so-called "spiral" configuration implementing flat membrane sheets, separated by spacers, rolled around a tube collecting the filtrate (that is to say the part of the fluid to be treated which has passed through the membranes, in contrast to the concentrate which is the part of the fluid which has not passed through these membranes and in which are concentrated the impurities held back by the membranes.
- a so-called "hollow fiber" configuration, in which the membranes appear in the form of bundles of capillary fibers.

Whatever the type of configuration, the modules (in general of a diameter of 8 inches and a length of 40 inches for industrial water treatment installations) are connected to each other, in principle in series, within so-called "pressure tubes". A complete nanofiltration system may comprise several pressure tubes mounted in parallel, conventionally fixed onto units (or skids), or even most often several units (or stages) each formed by a plurality of tubes.

The problem which arises in practice is that of detecting a defect in the integrity of a module, or of a system constituted by a plurality of modules, of which the origin lies either with the membrane themselves, or with the joints, and which results in a passage of the fluid directly from the dirty side of the membrane (concentrate) to the clean side (filtrate) through the pierced membrane or deficient joint.

Thus there are two main categories of checking methods applied to models taken individually, that is to say methods of detecting the modification of the integrity of modules for nanofiltration or reverse osmosis.

- methods implementing quality control of the water produced, i.e. of the filtrate (in particular by measurement of conductivity, or by bacteriological analyses),
- methods implementing leak detection using a physical process (for example measurement of throughput, or measurement of low pressure).

These methods are implemented on the filtration modules taken individually and generally placed on test-beds; they cannot be used to locate defects in connections within a system in operation.

The method may also be cited of leak detection by noise measurement proposed in document WO99/44728, but this method is not applicable to reverse osmosis nor to nanofiltration, the latter two methods requiring operation in tangential flow mode of the membranes. This is because this mode uses higher pressures and speeds, and consequently the noises of leaks cannot be distinguished from ambient noise.

Methods also exist which apply to overall systems of modules; these methods in principle use measurements of conductivity of the water produced by the systems. Thus, for the desalination of sea water by reverse osmosis, a measurement of conductivity is generally sufficient. However, for nanofiltration membrane systems, the measurement of conductivity of the water produced by the systems does not enable defects to be detected with the necessary precision. This is because, by nature, nanofiltration lets through a high number of salts such as calcium, chlorides, nitrates, etc. without this being attributable to a defect in the integrity of the system.

SUMMARY OF THE INVENTION

The object of the invention is to alleviate the drawbacks of the known methods, by virtue of a method making it possible to detect a leak, in particular of living microorganisms (such as bacteria, viruses, protozoa, and especially Cryptosporidium and Giardia), through a nanofiltration or reverse osmosis module, or in a system formed from a plurality of such modules, without cessation of production, this detection able to be carried out pseudo-continuously, that is to say in a regular manner, in barely a few minutes, in a simple and reliable manner, in practice by a sample measurement of concentration.

In fact the invention is based on the discovery that it is very generally possible to choose, in the fluid to be filtered, a compound of which the concentration is normally very low in the filtrate in the absence of any leak, but for which the concentration increases very rapidly in case of failure of a membrane or a connection joint, this compound being such that its concentration increases, in case of degradation of the membranes or of the joints, sooner than the concentration of living germs.

This is because nanofiltration or reverse osmosis membranes are not adapted to eliminate matter in suspension. On the contrary, these membranes must be supplied with water for which the non-dissolved particulate content is already very low. As particles are absent at the input, it is thus not possible to use measurements linked to matter in suspension to detect leaks (turbidity, counting of particles, matter in suspension, etc.)

Nevertheless, nanofiltration or reverse osmosis membranes are used to separate dissolved matter. The size range of the molecules kept back extends from organic macromolecules to ions. Greater or lesser separation of dissolved matter is ensured as a function of the separation power of the membrane (very great for inverse osmosis, less great for nanofiltration).

For inverse osmosis membranes, the holding back of salts, of all kinds, is higher than 90%. For the most "open" membranes of the nanofiltration range, the holding back of salts is a function of the quality of the water at the input (Donnan effect), of the concentration of the salts, of their hydration, and of their size. It is common, for the latest generations of nanofiltration membranes, that for example more than 50% of calcium and hydrogen carbonates to pass through the membranes. For these membranes, an overall measurement of the quantity of salt in the water produced (for example by conductivity) does not enable leaks to be detected.

Nevertheless, certain polyvalent ions, such as sulfates and iron are always perfectly held back by the membranes, whether they be nanofiltration or reverse osmosis membranes. When a leak occurs in the system, the concentration of these polyvalent ions thus becomes greater than that in a system that is sound.

For the most "open" nanofiltration membranes the possible ranges for passage of analyzable compounds expressed in % are described in table 1 which gives, by way of example of the use of nanofiltration for a given natural water, the indication of the degree of passage through nanofiltration membranes of various compounds identified. In this table, the passage of a compound is formulated as follows:

Passage (%)=100×(concentration of the compound in the filtrate/concentration of the compound on the concentrate side)

The concentration of the compound on the concentrate side is defined as the mean between the input of the tube and the concentrate of the tube.

It is worth noting that it is possible to identify a compound present in the water supplying the membranes but normally kept back to a high proportion by those membranes, and consequently capable of being detected when a concentrate/filtrate leak occurs and which is easily measurable in the field. It is even generally possible to identify such a compound which is both present in a large quantity in the supply water as well as being strongly rejected by the membranes (least possible passage).

Ions or compounds such as chlorides and bicarbonates which are easy to measure have a level of passage which may be judged to be too high. Furthermore, the level of passage of certain compounds is strongly linked to the pH of the water: this is the case in particular with carbonated compounds which may pass in the form of carbonic acid, idem for silicic or boric acid which are molecular in their acid form and thus pass through the membranes in contrast to their ionic forms.

However, the sulfate ion has numerous advantages:
it is naturally present in sea water and surface water,
being an ion of a strong acid, its form remains unaltered whatever the pH of the water,
measuring its concentration is rapid and undemanding,
sulphuric acid is often added to adjust the pH at the input to the membranes, which further increases the quantity of sulfate ions on the concentrate side of the membranes.

Moreover, it has been possible to verify that, in the case of leakage in a nanofiltration or reverse osmosis membrane, a compound such as a sulfate begins to be detectable before a detectable quantity of micro-organisms passes through the defect in the membrane or the connection joints.

Consequently, the invention provides a method of checking the integrity of a system of nanofiltration or reverse osmosis modules adapted for the treatment of a supply fluid and of detecting leaks of living micro-organisms, each module comprising nanofiltration or reverse osmosis membranes and connection joints of these membranes, comprising steps consisting of:
choosing a dissolved compound in the supply fluid which is in significant quantity but which is normally strongly kept back by the membranes,
measuring the value of the concentration of the compound in a downstream zone of a module of that system,
comparing this measured value with a reference value, and
recognizing the existence of a defect in that zone of the system when that measured value is greater than the reference value.

Preferably, when the system comprises at least one plurality of modules mounted in parallel, this method comprises steps consisting of:
measuring the value of the concentration of that dissolved compound in similar downstream zones of each module of that plurality,
comparing these measured values for each module,
identifying those of these values which are the least, and identifying as reference value a value at least approximately equal to those least values,
recognizing the existence of a defect in one of the modules mounted in parallel when the measured value for that module is greater than that reference value. This makes it possible to detect, without a reference being given in advance, that one of the modules mounted in parallel which, the case arising, comprises a defect.

Naturally this applies to the case in which the modules mounted in parallel each form part of a series of modules. Thus according to another preferred aspect of the invention, the general method defined above is characterized in that, the system comprising a plurality of series of modules mounted in parallel, that method comprises steps consisting of:
measuring the value of the concentration of that dissolved compound in similar zones of each series,
comparing these measured values for each series,
identifying those of these values which are the least, and identifying as reference value a value at least approximately equal to those least values,
recognizing the existence of a defect in one of these series when the measured value for that series is clearly greater than that reference value.

Advantageously, to identify the element in that series which comprises the defect, the method of the invention is characterized in that it further comprises steps consisting of:

measuring the value of the concentration of that dissolved compound in a plurality of zones chosen along the series of modules, for each value of the concentration measured for a given zone, taking a reference value substantially equal to the value of the concentration measured for the zone situated immediately upstream of that given zone or, if lacking, of the zone situated immediately downstream of it, and recognizing the existence of a defect in a given zone when the value which is measured there is greater than the associated reference value.

In this last case, it is advantageous for the zones chosen along the series of modules to comprise at least one zone downstream of each module and one zone of each connector connecting a module to the following one. Thus each element of the series is actually tested.

In an advantageous manner, to obtain a measurement representative of the whole series of modules considered, the value of the concentration of that dissolved compound is measured in a sample of fluid taken from a zone containing fluid coming from each module of that series.

The above applies to the case of a series of modules independently of any prior detection of defect in it, in which case the method is characterized in that, the system comprising at least one series of modules, this method comprises steps consisting in:

measuring the value of the concentration of that dissolved compound in a plurality of zones chosen along the series of modules, for each value of the concentration measured for a given zone, taking a reference value substantially equal to the value of the concentration measured for the zone situated immediately upstream of that given zone or, if lacking, of the zone situated immediately downstream of it, and recognizing the existence of a defect in a given zone when the value which is measured there is greater than the associated reference value.

In this case too, as in the case of several series of modules, the method of the invention is advantageously characterized in that the zones chosen along the series of modules comprises at least one zone downstream of each module and one zone of each connector connecting a module to the following one.

Preferably, when the system comprises at least one series of modules, the value of the concentration of that dissolved compound is measured in a sample of fluid taken from a zone containing fluid coming from each module of that series.

It appears clearly from the explanations given with respect to table 1 that it is especially advantageous to choose sulfate as the compound of which the concentration is measured.

Aims, features and advantages of the invention will appear from the following description, given by way of non-limiting illustration with reference to the accompanying drawings in which:

DETAILED DESCRIPTION OF THE INVENTION

The invention is described below, in a preferred embodiment, in relation to a system comprising a plurality of successive stages (or units), each formed of tubes mounted in parallel, each of the tubes comprising modules (6 in the example considered, another typical value being 7) with the aim of checking the integrity of the system of nanofiltration or reverse osmosis membranes and of detecting leaks of living micro-organisms (such as bacteria, viruses, protozoa, and especially Cryptosporidium and Giardia) through modules constituted by sheets of rolled (spiral) membrane or having hollow fibers and by joints. The method comprises the steps consisting of:

taking a sample of water in the smallest assembly constituted by the filtrate tubes and the interconnectors (generally a pressure tube equipped with 5 to 7 modules coupled by connections), comparing the value of sulfate ions or any other strongly rejected compound with the values of the other tubes placed at the same level of the system (also termed stage). An example is given in FIG. 3.

Figure 2A:
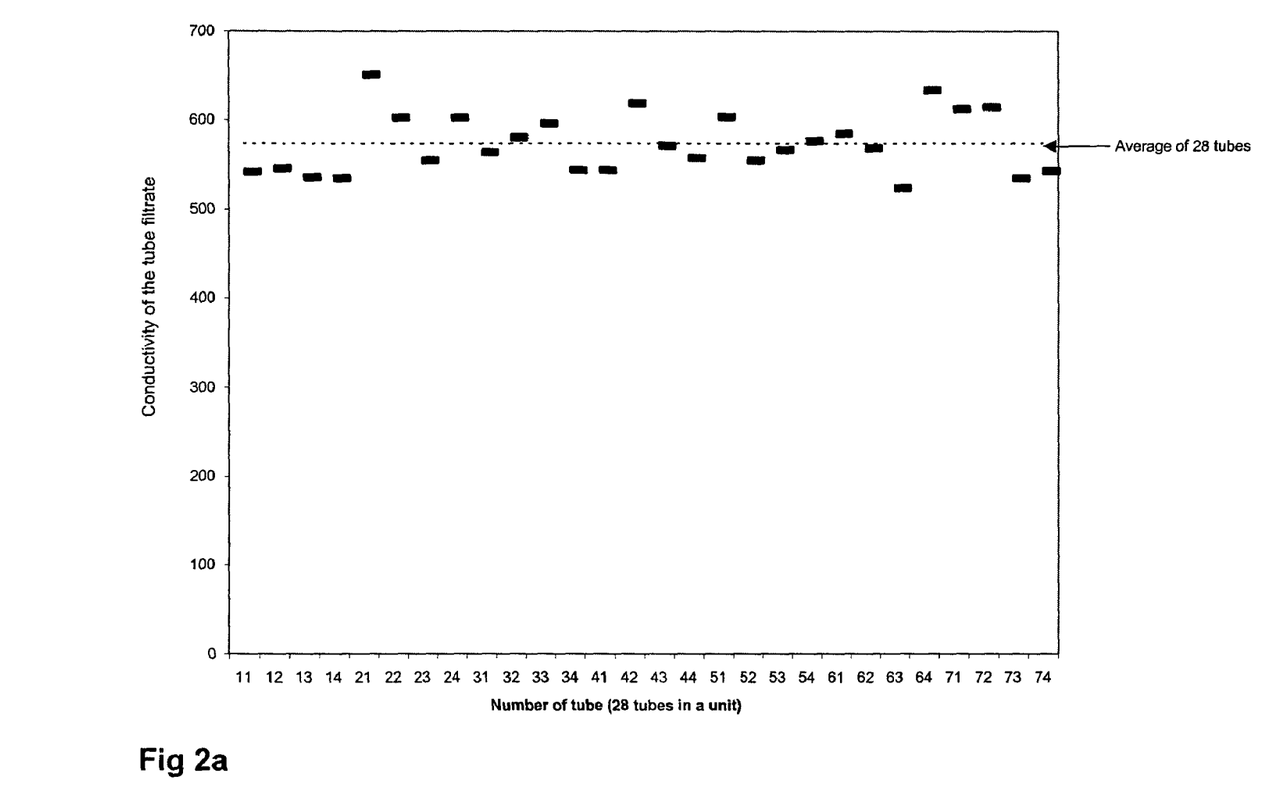
FIG. 2a is a graph showing the conductivity of 28 pressure tubes of the third stage.
Figure 2B:
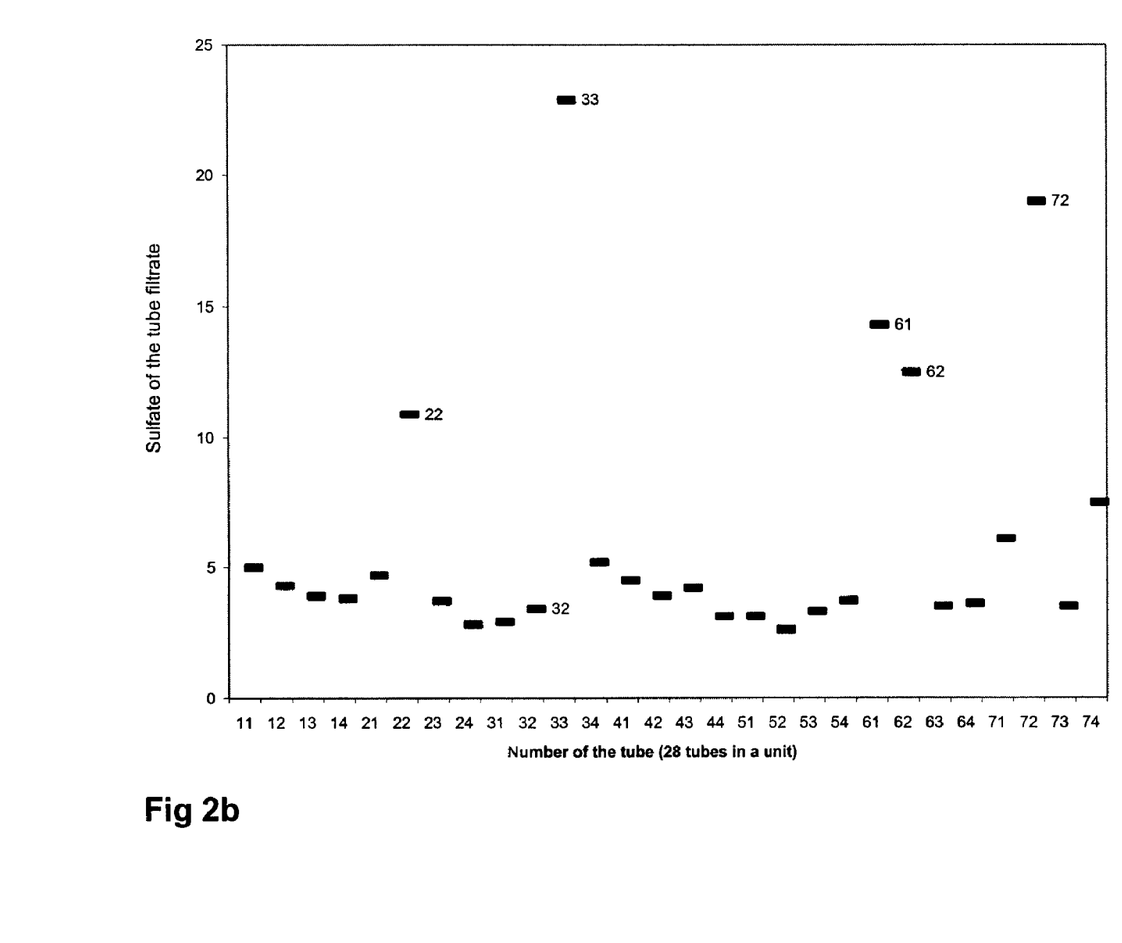
FIG. 2b is a graph showing the sulfate concentration in mg/l at the output of the same pressure tubes as in FIG. 2a, FIG. 3 is a graph showing the evolution in the sulfate concentration, in mg/l, along a tube formed from 5 modules.

If the sample of water thus taken has a concentration of strongly rejected compound (preferably sulfate) in the range of the tubes having a low concentration of strongly rejected compound, the tube has no defect of integrity, (see FIG. 2b, the case of tube No. 32 for example).

Figure 1A:
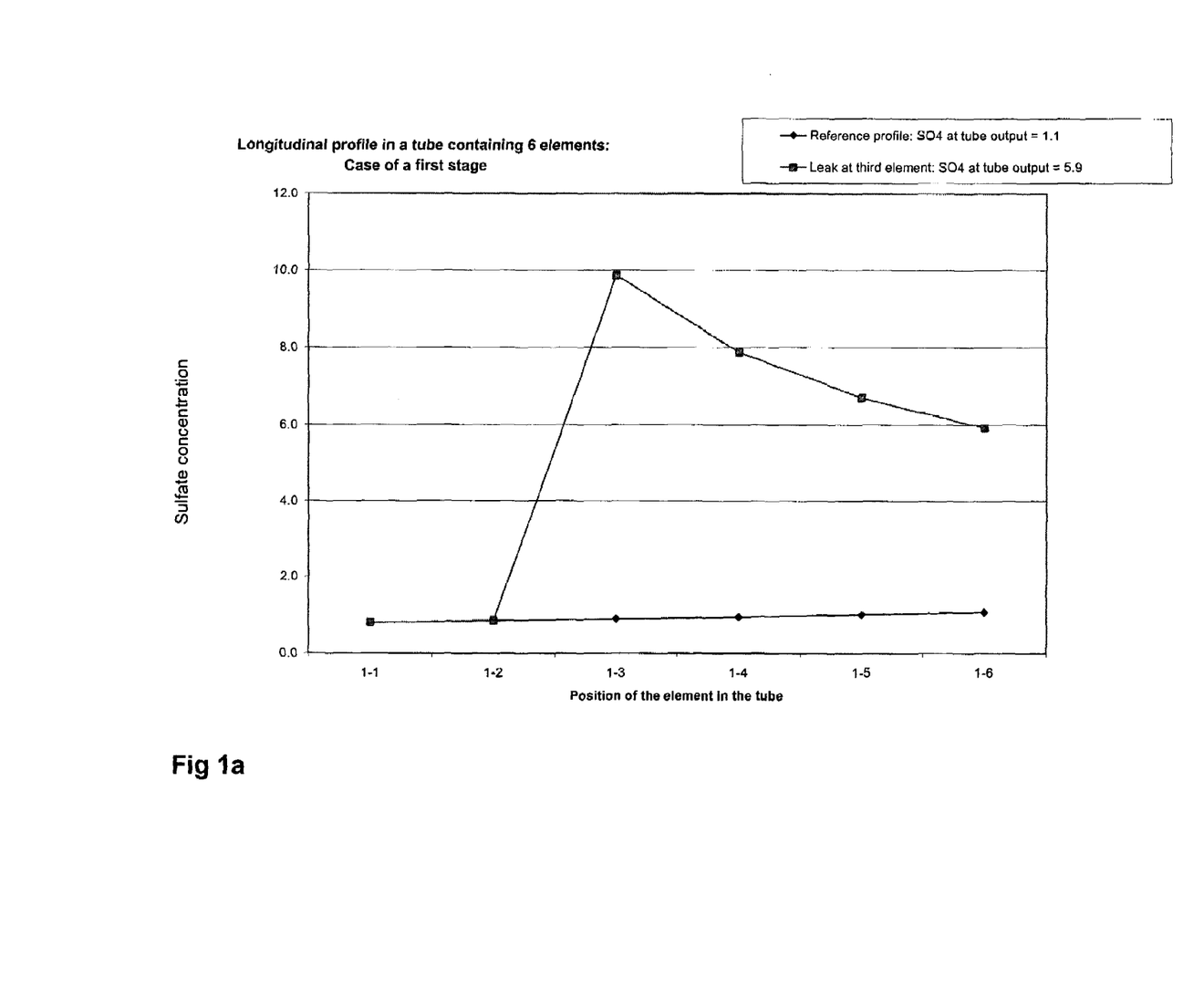
FIG. 1a is the sulfate concentration profile (in mg/l) along a series of modules, or a tube, of the first stage of a nanofiltration system having a leak at the connection between the second and third modules.
Figure 1B:
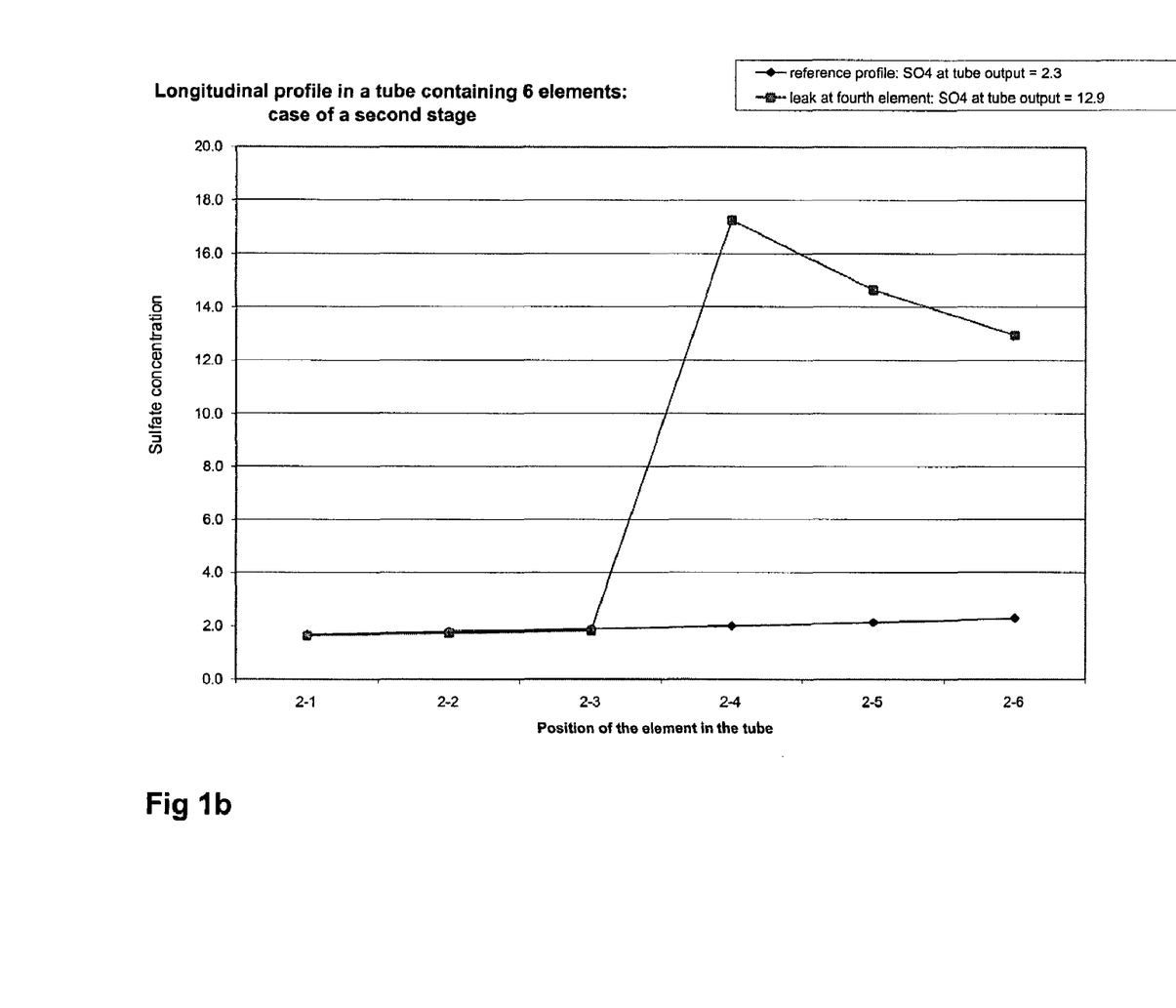
FIG. 1b is the sulfate concentration profile (in mg/l) along a series of modules, or a tube, of the second stage of that system, having a defect at the connection of the third and fourth modules.
Figure 1C:
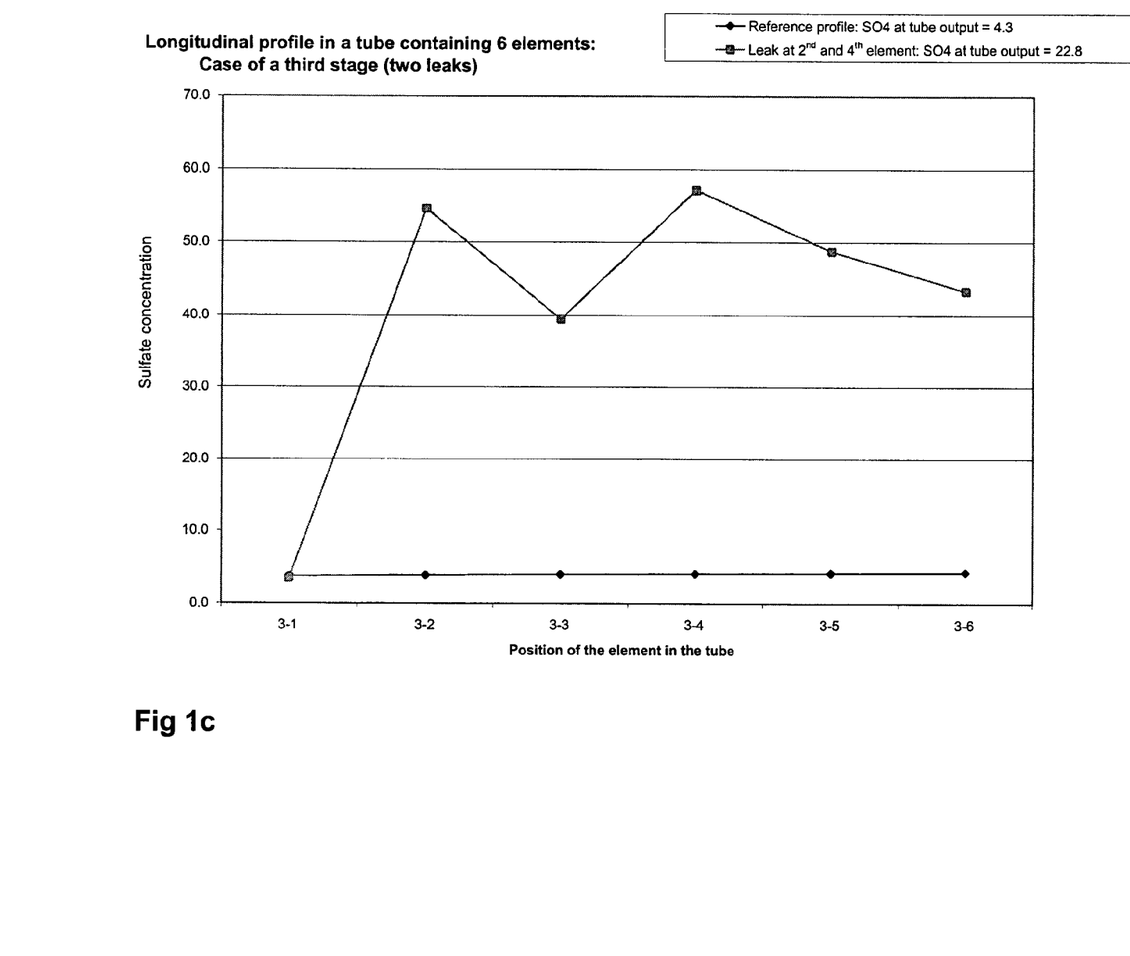
FIG. 1c is the sulfate concentration profile (in mg/l) along a series of modules, or a tube, of the third stage of that system, having a defect at the connection of the first and second modules and at the connection of the third and fourth modules.

If the sample of water thus taken has a concentration of strongly rejected compound (preferably sulfate) greater than all the tubes having a low concentration of strongly rejected compound, proceed with a probing operation which will make it possible to detect the defective module or the defective joint, as described in the next point, with the aid of a probe, take a plurality of sample of water along the assembly constituted by the tubes of filtrate and the interconnectors, measure the concentration of strongly rejected compound (preferably the sulfate) in the samples following the protocol described for example in the NFT90-040 standard or any other field method (kits commercially available).

trace the longitudinal concentration profile along the tube (see FIGS. 1a, 1b, and 1c).

Figure 3:
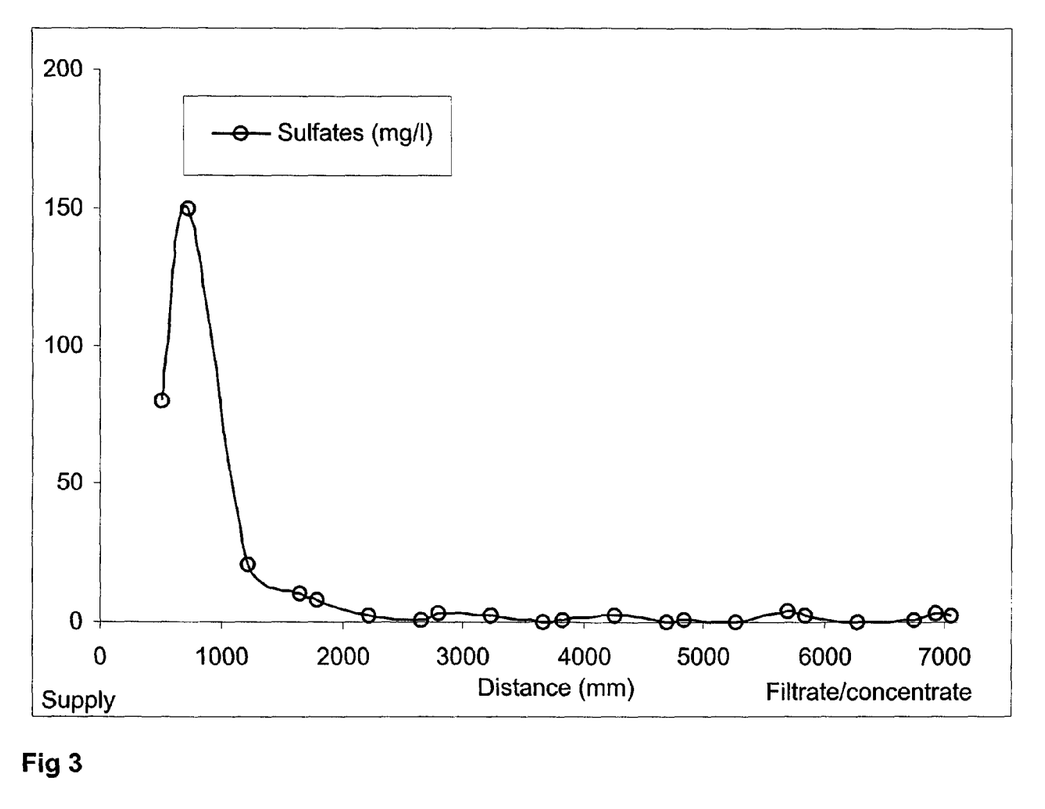

The longitudinal concentration profile along the tube follows an outline as shown in FIG. 3. The longitudinal reference profile may be either measured on a tube for which the sulfate concentration is least, or else calculated.

According to the operation it is possible to foresee different uses among which the following is cited in particular.

By way of example, the method described above was applied to the nanofiltration plant at Méry-sur-Oise which comprises 8 nanofiltration lines, each producing 17500 m$^3$ of water per day and comprises 1140 nanofiltration modules each of approximately 37 m$^2$. The nanofiltration modules are inserted in pressure tubes on the basis of 6 modules per tube. There are thus 1520 pressure tubes in the Méry-sur-Oise plant. The modules are arranged in three nanofiltration stages organized as follows:

The first stage receives the water to be treated of which the sulfate concentration is between 50 and 100 mg/l approximately, The second stage receives the concentrate from the first stage, The third stage receives the concentrate from the first stage, A systematic measurement of the sulfate concentration in the filtrate of the 1520 pressure tubes has enabled errors of assembly to be corrected, which consisted essentially of:

1. The replacement of 11 flattened or worn interconnecting joints,
2. The installation of 20 missing joints
3. The installation of 4 missing connectors
4. The changing of four broken membrane elements.

If they are not corrected, these assembly errors may result in bad fluid-tightness between the concentrate and filtrate compartments of the pressure tubes, letting a flow of concentrate through into the filtrate collectors of the tubes. The concentrate may be charged with undesirable compounds, above all bacteria.

These assembly errors cannot be detected by conductivity measurements of the water produced by the pressure tubes since nanofiltration naturally lets through certain ions (such as chlorides, calcium and hydrogen carbonates), the conductivity of the filtrate of the tubes is high in comparison with that produced by reverse osmosis. An example is given in FIG. 2a where a unit of 28 tubes (third stage) has been the subject of conductivity measurement. No tube has an atypical conductivity in comparison with the other tubes of the unit.

By contrast, a measurement of sulfate in the filtrates of the same tubes showed that tubes No. 22, 33, 61, 62 and 72 were atypical, they were producing water of which the sulfate concentration was significantly higher (cf. FIG. 2b).

Table 2 and FIG. 3 show the sulfate results on probing the pressure tube No. 61 of unit 4, the sulfate leak being situated at the supply connector of the first membrane. The temperature of the water was 4° C.

Bacteriological measurements of the water according to the NFT90-414 standard carried out at the output of the pressure tubes during campaigns for correction of defects in fluid-tightness enabled it to be shown that when the tubes have atypical sulfate values (in comparison with the other tubes of the unit as is shown in FIG. 2b), leakage of germs may appear.

The results of the analyses arising from the NFT90-414 standard have been the subject of an arbitrary rating which makes possible a comparison of samples with each other, the scale being the following:

Presence of coliform colony positive:

Rating 10=1 colony

Rating 20=2 colonies

Rating 30=3 colonies, etc.

Absence of coliform colony positive and absence of non-pathogen interfering flora:

Rating 0

Absence of coliform colony positive but presence of non-pathogen interfering flora (saprophytes):

Rating 1=0 to 10 saprophytes

Rating 2=11 to 50 saprophytes

Rating 3=51 to 100 saprophytes

Rating 4=greater than 100 saprophytes

Rating 5=culture medium covered over.

The ratings are added together when the results include both positive coli responses and saprophytes, for example a rating of 23 corresponds to two coliforms counted as well as 53 saprophytes counted.

The bacteriological measurements can only be interpreted statistically since the positive responses can be biased (contamination) as well as the negative responses since the sampling is made on 100 ml sample.

Figure 4:
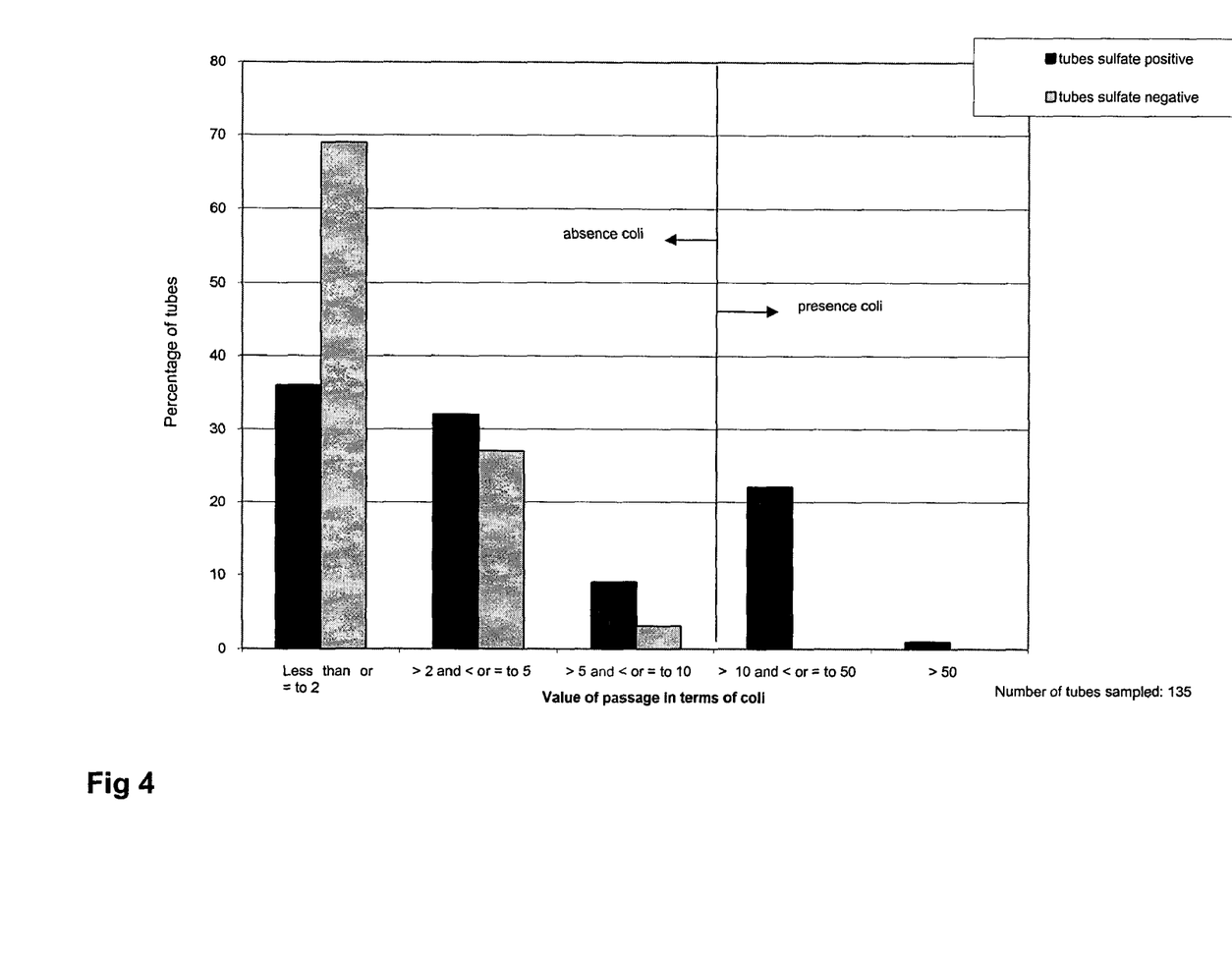
FIG. 4 is a graph showing the bacteriological analysis in the filtrate of the tubes of the system.

The results of 135 samples carried out in the filtrate of tubes before and after correction are given in FIG. 4.

Figure 5:
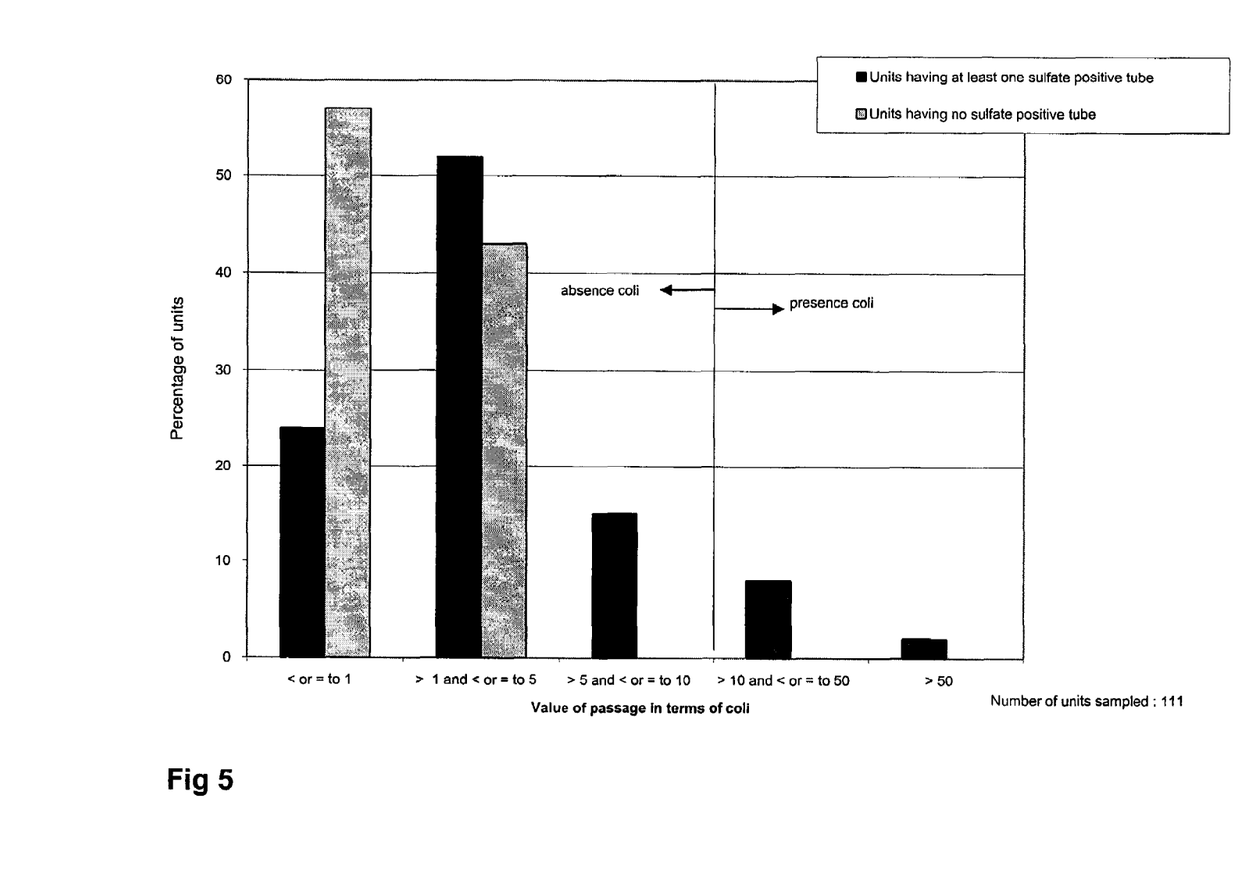
FIG. 5 is a graph showing the bacteriological analysis in the filtrate of the units or stages of that system.

At the units, which are constituted by 28 or 54 tubes in the application at Méry-sur-Oise, the consequence of one or more tubes of which the fluid-tightness is not absolute is represented in FIG. 5.

TABLE 1

| Compound | Passage | Passage too high | Function of the pH | Little present in natural water | Insufficient precision of analysis |
| --- | --- | --- | --- | --- | --- |
| Aluminium | 10% to 50% | x | ? | x | x |
| Barium, strontium | 10% to 50% | x | | x | x |
| Calcium | 10% to 60% | x | | | |
| Chlorides | 50% to 80% | x | | | |
| Conductivity | 20% to 60% | x | | | |
| Organic Carbon | 0% to 20% | x | | | x |
| Copper | 0 to 5% | | | x | |
| Fluoride | 30% to 50% | x | | | |
| Iron | 0 to 5% | | | x | x |
| Bicarbonates | 10% to 60% | x | x | | |
| Potassium | 40% to 70% | x | | x | |
| Magnesium | 10% to 40% | x | | | |
| Manganese | Up to 40% | x | | x | |
| Sodium | 50% to 80% | x | | | |

TABLE 1-continued

| Compound | Passage | Passage too high | Function of the pH | Little present in natural water | Insufficient precision of analysis |
|---|---|---|---|---|---|
| Ammonium, nitrites and nitrates | 50% to 80% | x | | x | x |
| Phosphate | 0 to 20% | | ? | x | x |
| Silica | Up to 80% | x | x | | x |
| Sulfate | Less than 5% | | | | |

TABLE 2

File membrane No. 1 Unit N .4 Tube No. 62
Temperature of the water: 4° C.

| Location | Length of probe introduced (mm) | 21/12/99 Sulfates (mg/l) |
|---|---|---|
| Sample origin | 0 | |
| Start connector input | 509 | 80 |
| End connector input | 725 | 150 |
| Middle membrane 1 | 1200 | 21 |
| Start connector 1 | 1635 | 10 |
| End connector 1 | 1782 | 8 |
| Middle membrane 2 | 2216 | 2 |
| Start connector 2 | 2651 | 1 |
| End connector 2 | 2798 | 3 |
| Middle membrane 3 | 3232 | 2 |
| Start connector 3 | 3667 | 0 |
| End connector 3 | 3814 | 1 |
| Middle membrane 4 | 4248 | 2 |
| Start connector 4 | 4683 | 0 |
| End connector 4 | 4830 | 1 |
| Middle membrane 5 | 5264 | 0 |
| Start connector 5 | 5699 | 4 |
| End connector 5 | 5846 | 2 |
| Middle membrane 6 | 6280 | 0 |
| Start connector output | 6747 | 1 |
| End connector output | 6926 | 3 |
| End filtrate tip | 7045 | 2 |

The invention claimed is:

1. A method of checking during operation the integrity of a system of nanofiltration or reverse osmosis modules adapted for a treatment of a supply water retaining living microorganisms and of detecting leaks of living microorganisms in said systems of modules, each module comprising nanofiltration or reverse osmosis membranes and connection joints of these membranes, comprising:
choosing in the supply water to be treated a dissolved compound which is in significant quantity in the supply water and which is normally strongly kept back by the membranes said compound being such that an increase in its concentration is detectable sooner than an increase in the concentration of the microorganisms passing through leaks is detectable, thus indicating degradation of the membranes or connection joints,
measuring the value of the concentration of the compound in a downstream zone of a module of that system,
comparing that measured value with a reference value, and
recognizing the existence of a defect which lets through a detectable quantity of microorganisms in that zone of the system when that measured value is greater than the reference value.

2. A method according to claim 1, wherein the system comprises at least a plurality of modules mounted in parallel, the method comprising:
measuring the value of the concentration of that dissolved compound in similar downstream zones of each module of said plurality of modules,
comparing said measured values for each module,
identifying those of said values which are the least values, and identifying as reference value a value at least approximately equal to said least values,
recognizing the existence of a defect in one of the modules mounted in parallel when the measured value for that module is greater than reference value.

3. A method according to claim 1, wherein the system comprises a plurality of series of modules mounted in parallel, said method comprising:
measuring the value of the concentration of that dissolved compound in similar zones of each series,
comparing said measured values for each series,
identifying those of said measured values which are the least values, and identifying as reference value a value at least approximately equal to said least values,
recognizing the existence of a defect in one of said series when the measured value for that series is clearly greater than that reference value.

4. A method according to claim 3, further comprising:
measuring the value of the concentration of said dissolved compound in a plurality of zones chosen along a series of modules,
for each value of the concentration measured for a given zone, taking a reference value substantially equal to the value of the concentration measured for the zone situated immediately upstream of that given zone or, it lacking, of the zone situated immediately downstream thereof, and
recognizing the existence of a defect in a given zone when the value which is measured there is greater than the associated reference value.

5. A method according to claim 4, wherein the zones chosen along the series of modules comprise at least one zone downstream of each module and one zone of each connector connecting a module to the following one.

6. A method according to claim 4 or 5, wherein the dissolved compound of which the concentration is measured is sulfate.

7. A method according to any one of claims 3 to 5, wherein the value of the concentration of that dissolved compound is measured in a sample of fluid taken from a zone containing fluid coming from each module of that series.

8. A method according to claim 7, wherein the dissolved compound of which the concentration is measured is sulfate.

9. A method according to claim 1, wherein the system comprises at least one series of modules, said method comprising:

measuring the value of the concentration of that dissolved compound in a plurality of zones chosen along the series of modules, for each value of the concentration measured for a given zone, taking a reference value substantially equal to the value of the concentration measured for the zone situated immediately upstream of that given zone or, if lacking, of the zone situated immediately downstream thereof, and recognizing the existence of a defect in a given zone when the value which is measured there is greater than the associated reference value.

10. A method according to claim 9, wherein the zones chosen along the series of modules comprise at least one zone downstream of each module and one zone of each connector connecting a module to the following one.

11. A method according to any one of claims 1, 9, or 10, wherein the system comprises at least one series of modules, and the value of the concentration of that dissolved compound is measured in a sample of fluid taken from a zone containing fluid coming from each module of that series.

12. A method according to any one of claims 1, 2 or 3, wherein the dissolved compound of which the concentration is measured is sulfate.

13. The method according to claim 12, wherein the sulphate concentration is less than approximately 100 mg/L.

14. A method according to claim 11, wherein the dissolved compound of which the concentration is measured is sulfate.

15. A method according to claim 9 or 10, wherein the dissolved compound of which the concentration is measured is sulfate.

* * * * *